(12) United States Patent
Song et al.

(10) Patent No.: US 8,822,678 B2
(45) Date of Patent: Sep. 2, 2014

(54) METHOD FOR SYNTHESIZING TEMSIROLIMUS

(71) Applicant: Tianjin Weijie Technology Co., Ltd., Tianjin (CN)

(72) Inventors: Honghai Song, Tianjin (CN); Long Tang, Tianjin (CN); Wei Chen, Tianjin (CN); Zheng Li, Tianjin (CN); Jinzhou Li, Tianjin (CN); Zhicun Sun, Tianjin (CN); Jiajin Feng, Tianjin (CN)

(73) Assignee: Tianjin Wiejie Technology Co., Ltd., Tianjin (CN)

( * ) Notice: Subject to any disclaimer, the term of this patent is extended or adjusted under 35 U.S.C. 154(b) by 0 days.

(21) Appl. No.: 13/933,118

(22) Filed: Jul. 1, 2013

(65) Prior Publication Data

US 2013/0296550 A1　Nov. 7, 2013

Related U.S. Application Data

(63) Continuation-in-part of application No. PCT/CN2011/074083, filed on May 16, 2011.

(30) Foreign Application Priority Data

Jan. 7, 2011　(CN) .......................... 2011 1 0002891

(51) Int. Cl.
*C07D 498/22* (2006.01)
*C07D 498/18* (2006.01)
*C07F 5/02* (2006.01)

(52) U.S. Cl.
CPC ................................. *C07D 498/18* (2013.01); *C07F 5/02* (2013.01)
USPC .......................................................... 540/456

(58) Field of Classification Search
USPC .......................................................... 540/456
See application file for complete search history.

(56) References Cited

U.S. PATENT DOCUMENTS 7,153,957 B2 * 12/2006 Chew et al. ................... 540/456

* cited by examiner

*Primary Examiner* — Bruck Kifle
(74) *Attorney, Agent, or Firm* — Matthias Scholl P.C.; Matthias Scholl

(57) ABSTRACT

A method for synthesizing temsirolimus, the method including: using a substituted boric acid to protect 2,2-dimethylol propionic acid to produce intermediate II; carrying out a reaction between the intermediate II and 2,4,6-trichlorobenzoyl chloride; carrying out condensation reaction between a resulting product and rapamycin to produce intermediate III; and finally using a diol to remove a protecting group from the intermediate III to yield temsirolimus.

5 Claims, 5 Drawing Sheets

METHOD FOR SYNTHESIZING TEMSIROLIMUS

CROSS-REFERENCE TO RELATED APPLICATIONS

This application is a continuation-in-part of International Patent Application No. PCT/CN2011/074083 with an international filing date of May 16, 2011, designating the United States, now pending, and further claims priority benefits to Chinese Patent Application No. 201110002891.0 filed Jan. 7, 2011. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 14781 Memorial Drive, Suite 1319, Houston, Tex. 77079.

BACKGROUND OF THE INVENTION

1. Field of the Invention

The invention relates to the field of medical technology, and more particular to a method for synthesizing temsirolimus.

2. Description of the Related Art mTOR kinase is an important protein to control cell proliferation, growth, and survival. As a medicine for treating kidney cancers, Temsirolimus is able to inhibit mTOR kinase, lower the level of some angiogenesis factors, such as the vascular endothelial growth factor, inhibit the growth of new vessels, and finally lead to the death of cancer cells.

A typical method for preparing Temsirolimus is shown in FIG. 2. The method includes: carrying out reaction between 2,2-dimethylol propionic acid and 2,4,6-trichlorobenzoyl chloride under the protection of 2,2-dimethoxypropane to yield an anhydride; condensing the anhydride with rapamycin, separating intermediate A-1, and finally removing a protecting group to yield Temsirolimus. However, the method has defects that it is difficult to separate a product from a by-product produced by synchronous esterification of 31- and 42-hydroxyl radicals, and the total yield is only 20%.

An improved synthetic method is shown in FIG. 3. The method includes: protecting the 31- and 42-hydroxyl radicals by trimethylchlorosilane; selectively removing a 42-protecting group to yield intermediate B-1; carrying out a condensation reaction between the intermediate B-1 and the anhydride; and finally removing a 32-protecting group to yield temsirolimus. Although the yield of the method is increased to 47%, the method has multiple reaction steps and a complicate process.

Further improvement is shown in FIG. 4, including: protecting 2,2-dimethylol propionic acid by phenylboronic acid, and removing the protecting group by 2-methyl-2,4-pentanediol to yield temsirolimus. And another improved method is shown in FIG. 5. The method includes: enzyme catalyzing rapamycin, carrying out reaction between 42-hydroxyl radical of rapamycin and alkyl group protected 2,2-dimethylol propionic acid, and removing the protecting group to yield temsirolimus. The method has high yield, but high production cost.

Thus, methods for synthesizing temsirolimus in the prior art are disadvantageous in low yield, multiple reaction steps, complicate process, and high production cost.

SUMMARY OF THE INVENTION

In view of the above-described problems, it is one objective of the invention to provide a method for synthesizing temsirolimus that has a simple process, low cost, and high efficiency.

To achieve the above objective, in accordance with one embodiment of the invention, there is provided a method for synthesizing a compound of formula I,

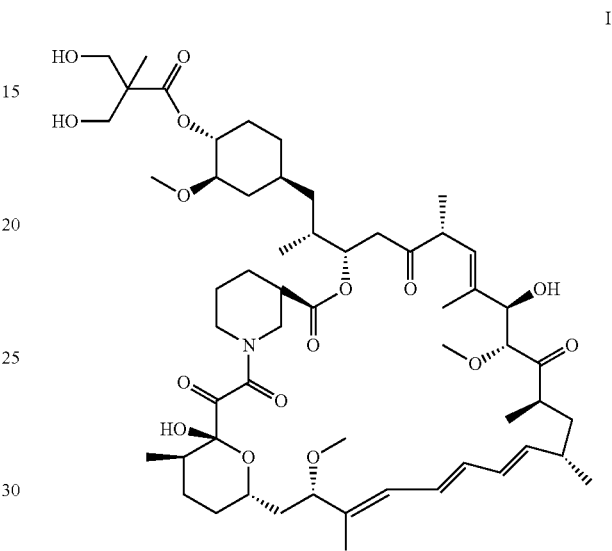

and the method comprises:

1) providing a raw material comprising 2,2-dimethylol propionic acid and a substituted boric acid; dissolving the raw material in tetrahydrofuran to form a solution; allowing the solution at room temperature to react; adding toluene to the solution, heating and refluxing the solution; and adding cyclohexane to the solution to yield intermediate II represented by the following formula:

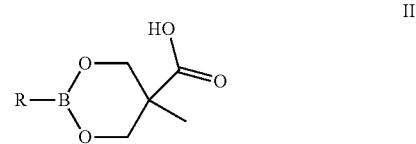

wherein, R represents a hydrogen atom, an alkyl group comprising between one and six carbon atoms, a cycloalkyl or substituent thereof comprising between one and six carbon atoms, an alkenyl comprising between one and six carbon atoms, an alkynyl comprising between one and six carbon atoms, a benzyl or a substituent thereof, an aromatic ring or a substituent thereof comprising between seven and twenty carbon atoms, or a heteroaromatic ring or a substituent thereof comprising between four and twenty carbon atoms;

2) dissolving the intermediate II in a first organic solvent; adding an alkali and 2,4,6-trichlorobenzoyl chloride, respectively, to the first organic solvent to yield a mixture; allowing the mixture to react in the presence of nitrogen gas at a temperature of between −20 and 40° C. for between 4 and 8 h; adjusting the temperature of the mixture to −10° C.; adding rapamycin and an acid binding agent to the mixture, allowing the mixture to react overnight at room temperature; and separating intermediate III represented by the following formula by using silica gel column chromatography:

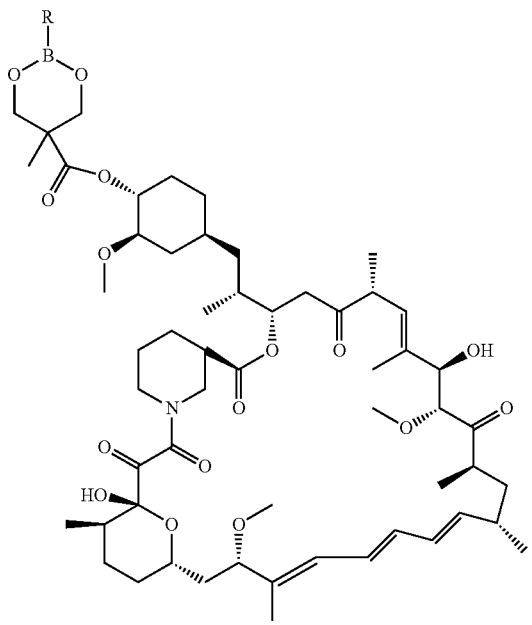

wherein, R represents the same structure as that of the intermediate II; and 3) dissolving the intermediate III in a second organic solvent, adding a diol to the second organic solvent to yield a mixed solution; allowing the mixed solution to react at a temperature of between −20 and 20° C. for between 8 and 14 h;

and precipitating and separating a resulting product by using silica gel column chromatography to yield temsirolimus.

In a class of this embodiment, the substituted boric acid is selected from the group consisting of ethylboronic acid, propylboronic acid, cyclohexylboronic acid, and benzylboronic acid. A molar ratio between 2,2-dimethylol propionic acid and the substituted boric acid is 1:1.

In a class of this embodiment, in step 2), a molar ratio between rapamicin, the intermediate II, and 2,4,6-trichlorobenzoyl chloride is 1:1-1.5:1-1.4. The first organic solvent is selected from the group consisting of toluene, benzene, xylene, ether, methyl tert-butyl ether, tetrahydrofuran, dichloromethane, chloroform, carbon tetrachloride, 1,2-dichloroethane, and ethyl acetate. The alkali is selected from the group consisting of triethylamine, N,N-diisopropylethylamine, and N,N-dimethylaniline. The acid binding agent is selected from the group consisting of pyridine, 4-dimethylaminopyridine (DMAP), 4-pyrrolidinopyridine, and N-methylimidazole.

In a class of this embodiment, the diol in step 3) is selected from the group consisting of 1,2-, 1,3-, 1,4-, 1,5-diol, and a $C_1$-$C_6$ substituted diol. A molar ratio between the intermediate III and the diol is 1:1-10. The second organic solvent is selected from toluene, benzene, xylene, ether, methyl tert-butyl ether, tetrahydrofuran, dichloromethane, chloroform, carbon tetrachloride, 1,2-dichloroethane, ethyl acetate, and acetone.

Advantages of the invention are summarized as follows: the method for synthesizing temsirolimus of the invention employs two-step reactions to yield the product, has a high yield of 54.8%, simplified synthetic steps and thus low production cost.

BRIEF DESCRIPTION OF THE DRAWINGS

The invention is described hereinbelow with reference to the accompanying drawings, in which.

DETAILED DESCRIPTION OF THE EMBODIMENTS

Figure 1:
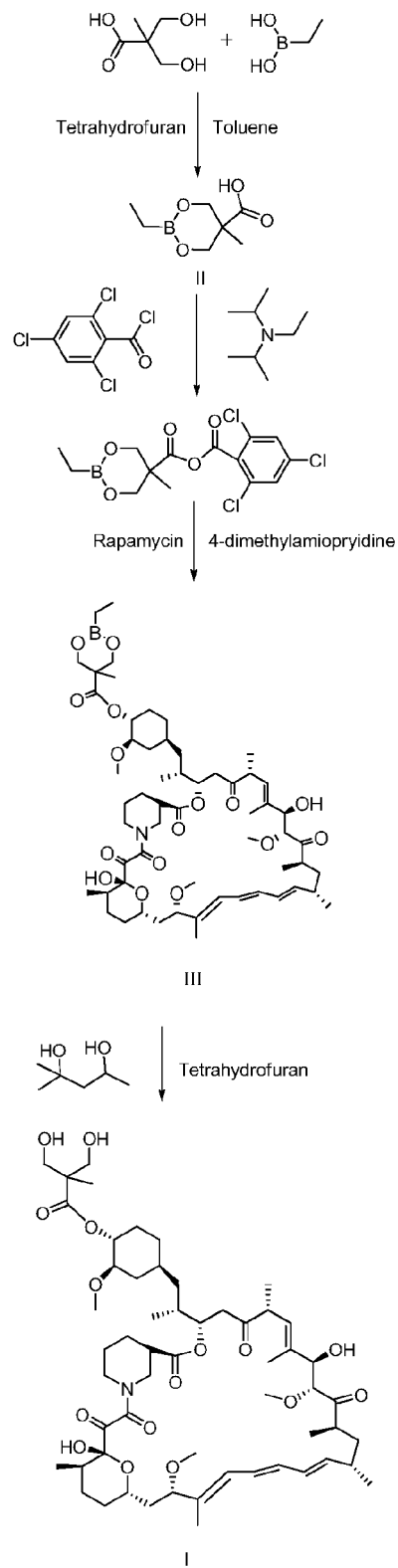
FIG. 1 is a synthetic route for temsirolimus in accordance with one embodiment of the invention.
Figure 2:
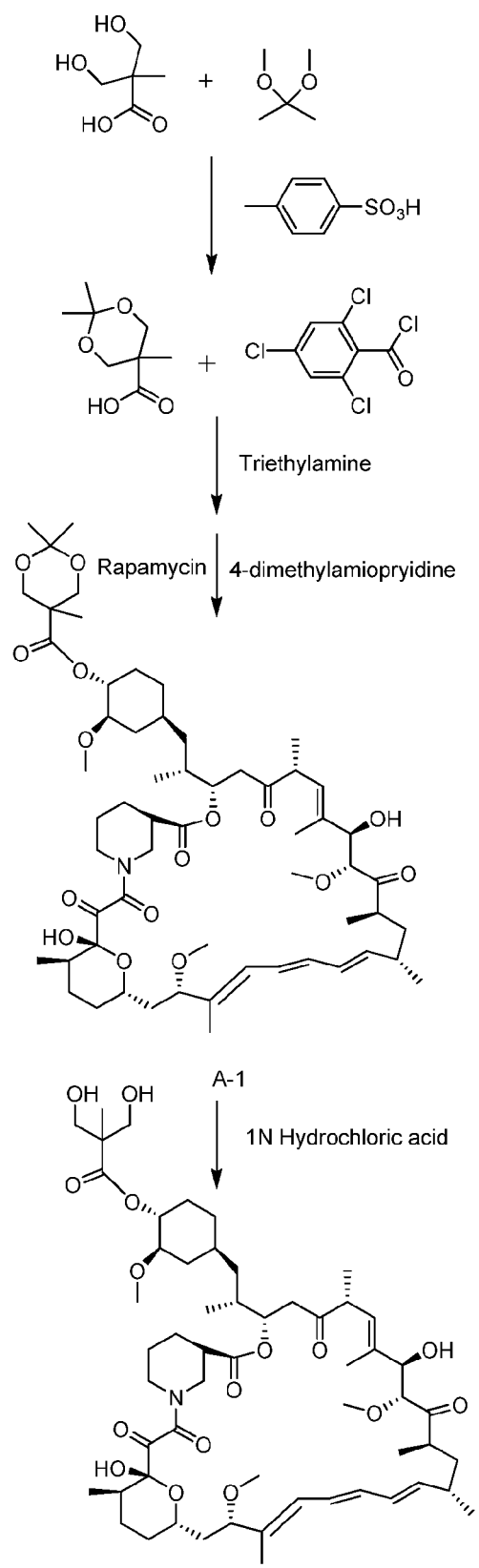
FIG. 2 is a first synthetic route for temsirolimus in the prior art.
Figure 3:
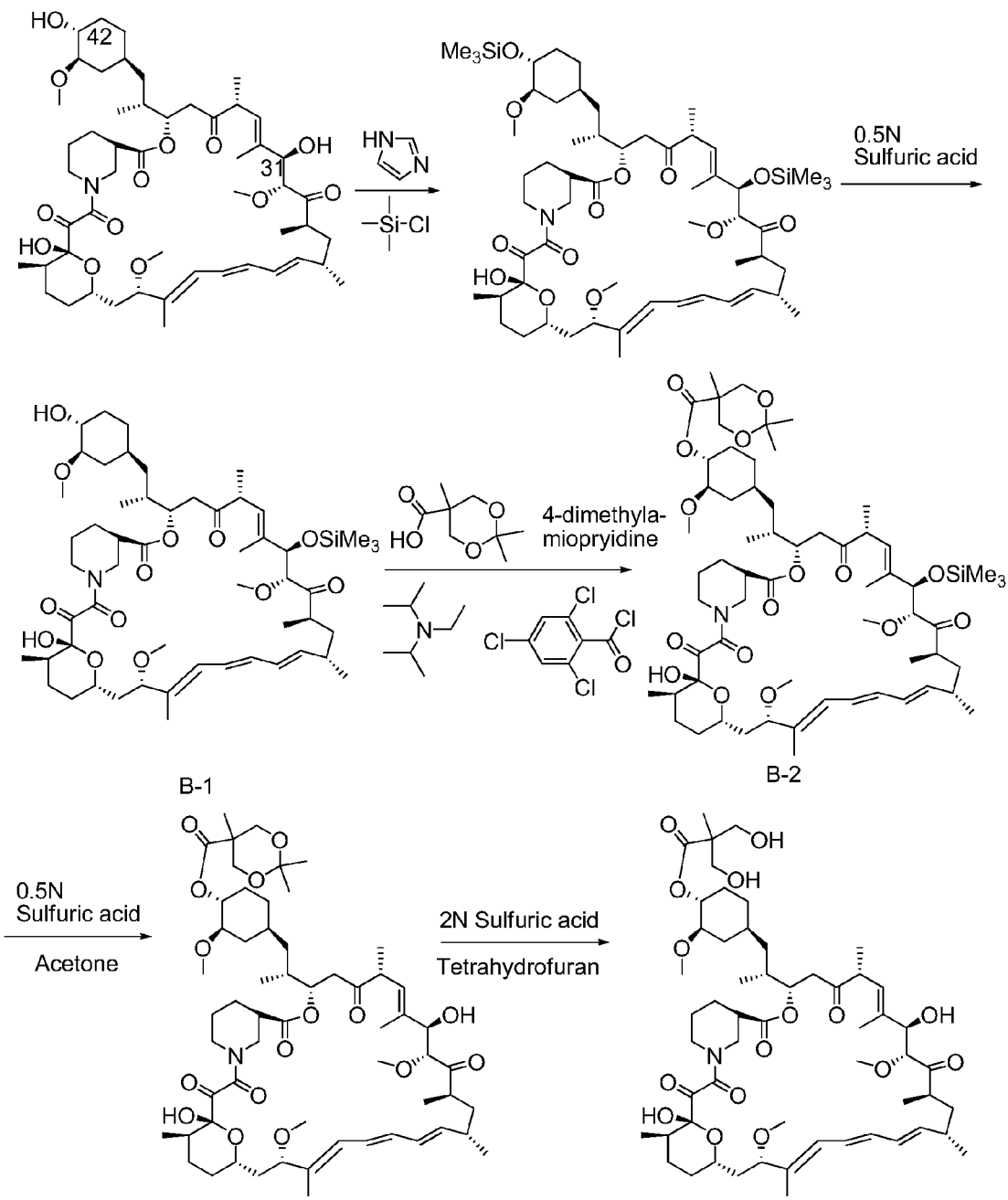
FIG. 3 is a second synthetic route for temsirolimus in the prior art.
Figure 4:
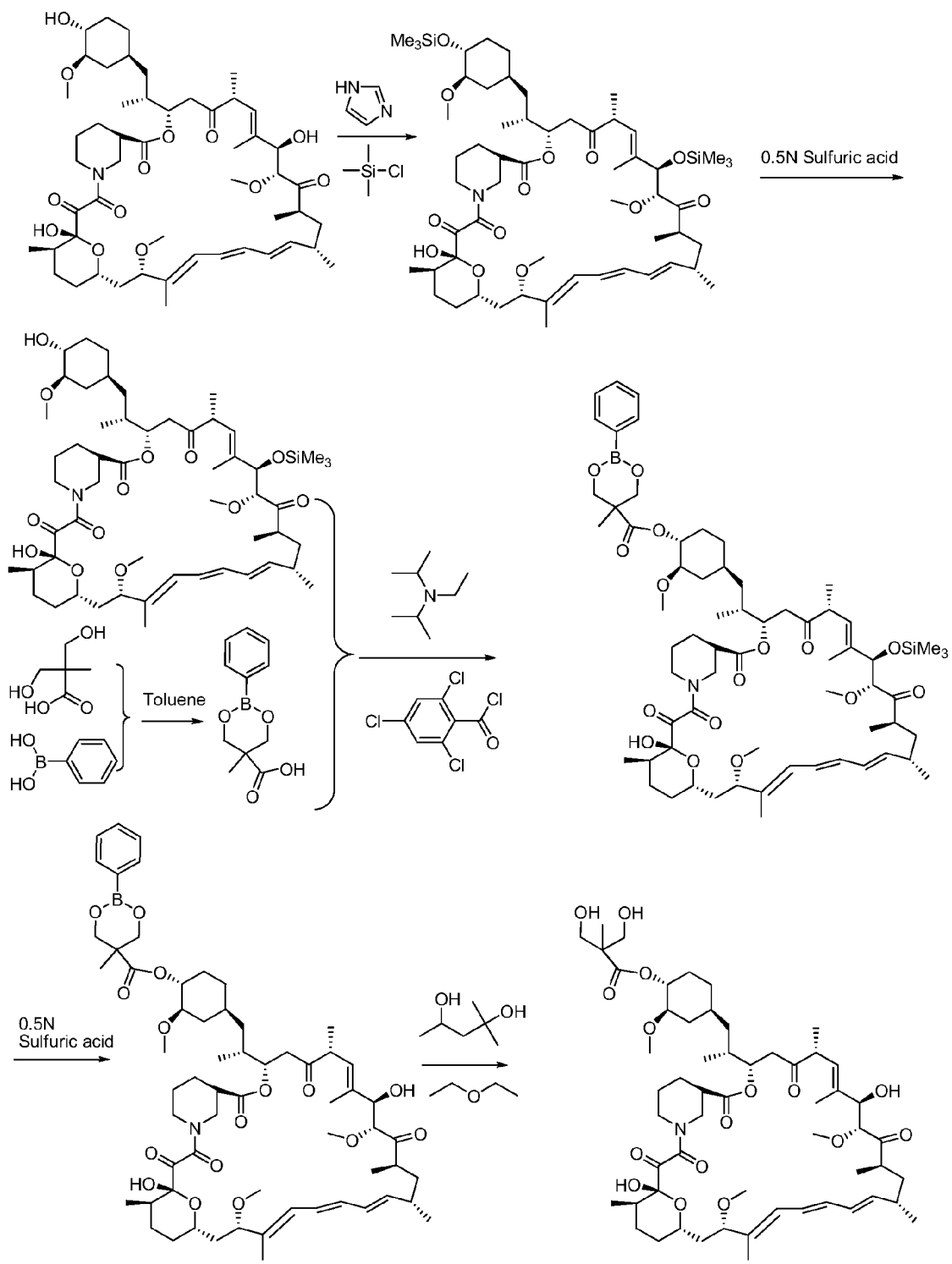
FIG. 4 is a third synthetic route for temsirolimus in the prior art.
Figure 5:
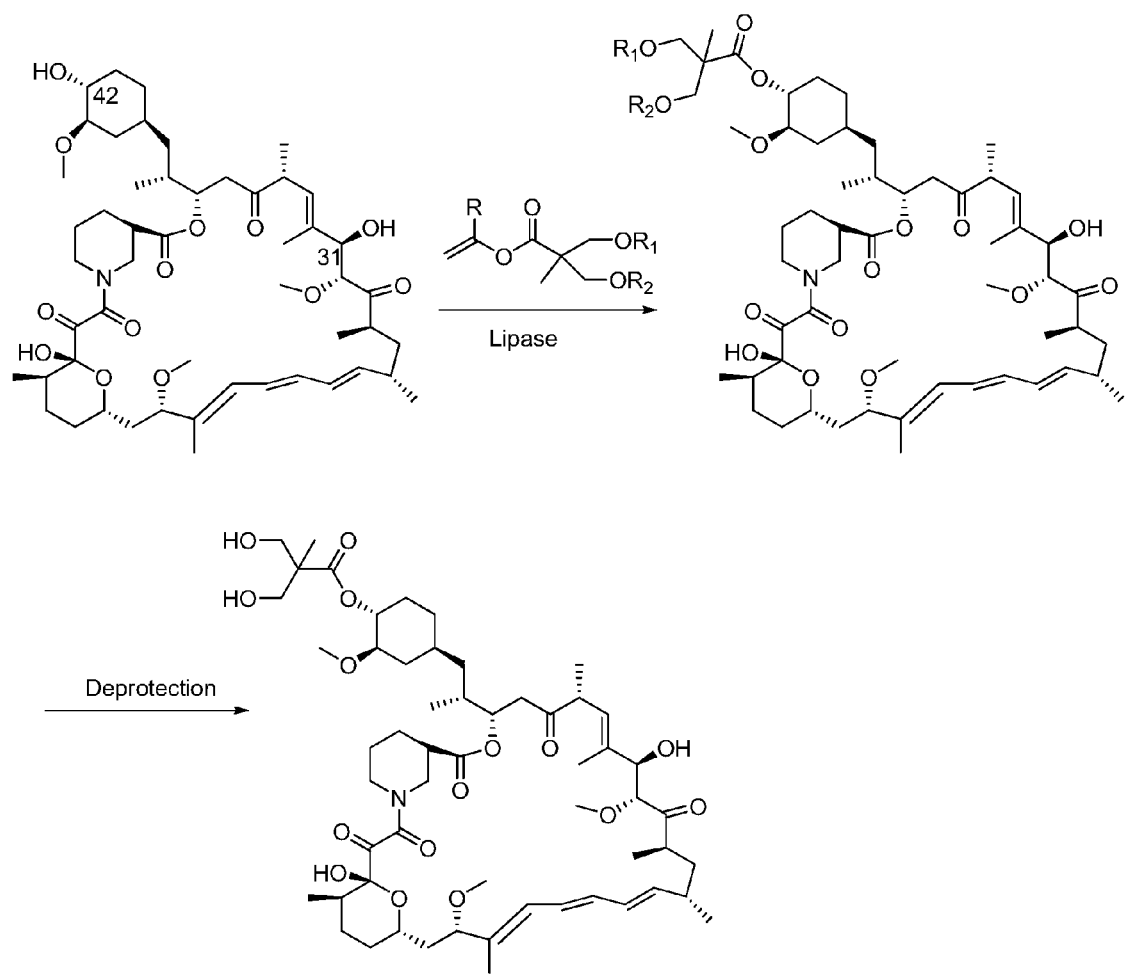
FIG. 5 is a fourth synthetic route for temsirolimus in the prior art.

For further illustrating the invention, experiments detailing a method for synthesizing temsirolimus are described below. It should be noted that the following examples are intended to describe and not to limit the invention.

Example 1

1) Add 13.36 g (0.098 mol) of 2,2-dimethylol propionic acid, 7.40 g (0.098 mol) of ethylboronic acid, and 50 mL of tetrahydrofuran to a 250 mL single-mouth bottle to yield a solution. Stir the solution at room temperature for 3 h, add 80 mL of toluene to the solution, heat and reflux the solution for 1 h. Cool the solution to room temperature, add 80 mL of cyclohexane to the solution until a solid substance begins to precipitate. Thereafter, heat the solution again until the solution is refluxed; cool the solution for allowing crystals to precipitate. Separate the crystals from the solution by filtration, and dry the crystals in the vacuum at the temperature between 70 and 75° C. to a constant weight. 11.97 g of intermediate II-1 is obtained, and the yield thereof is 71.0%.

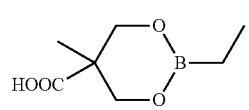

II-1

2) Add 0.24 g (1.42 mmol) of the intermediate II-1, 20 mL of dichloromethane, 0.28 g (2.18 mmol) of N,N-diisopropylethylamine, and 0.32 g (1.31 mmol) of 2,4,6-trichlorobenzoyl chloride to a 100 mL four-mouth bottle to yield a reaction solution. Stir the solution in the presence of nitrogen gas at the temperature of 14° C. for 4 h. Cool the reaction solution to the temperature of −10° C., add 1.00 g (1.09 mmol) of rapamycin and 0.27 g (2.18 mmol) of DMAP to the reaction solution, and heat the reaction solution to the temperature of 14° C. for reaction. After the reaction lasts for 14 h, add 30 mL of water to the reaction solution while stirring to form a mixture. Thereafter, transfer the mixture to a separating funnel for separating an organic phase from a water phase. Wash the organic phase by using a 2N sulfuric solution (10 mL×2), water (10 mL), a 5% sodium bicarbonate aqueous solution (10 mL), and saturated brine (10 mL), respectively, and dry the organic phase by using anhydrous magnesium sulfate. Filter, precipitate, and separate a resulting product by using silica gel column chromatography. 0.31 g of a white solid intermediate III-1 is obtained, and the yield thereof is 74.8% (according to the amount of rapamycin participating in the reaction).

III-1

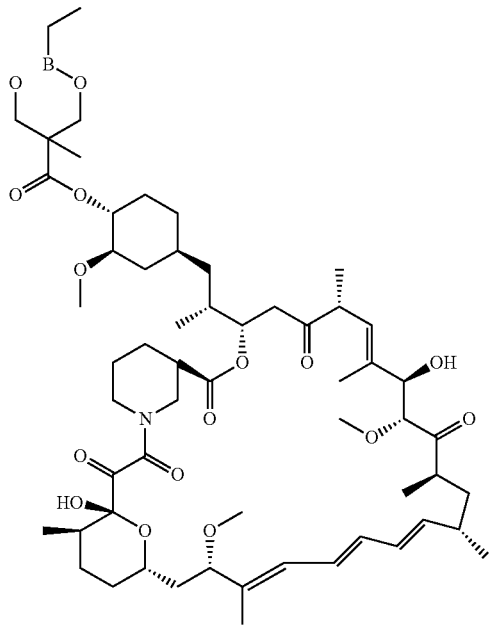

3) Add 0.31 g (0.287 mmol) of the intermediate III-1, 10 mL of tetrahydrofuran, and 0.08 g (0.678 mmol) of 2-methyl-2,4-pentanediol, respectively, to a 100 mL single-mouth bottle to yield a mixed solution. Stir the mixed solution overnight at the temperature of 14° C. for reaction. After 14 h of the reaction time, precipitate and separate a resulting product by using the silica gel column chromatography (between 200 and 300 mesh, an eluent comprising petroleum ether and acetic ether according to a ratio of 1:1). 0.22 g of white solid temsirolimus is obtained, and a yield thereof is 73.3%. MS: [M+Na] $^+$1052.6; $^1$H NMR (CDCl$_3$, 300 MHz): 4.70 (m, 1H), 3.86 (d, 2H), 3.81 (d, 2H), 1.12 (s, 3H).

Example 2

1) Add 13.36 g (0.098 mol) of 2,2-dimethylol propionic acid, 12.54 g (0.098 mol) of cyclohexylboronic acid, and 50 mL of tetrahydrofuran to a 250 mL single-mouth bottle to yield a solution. Stir the solution at room temperature for 3 h, add 80 mL of toluene to the solution, heat and reflux the solution for 1 h. Cool the solution to room temperature, add 80 mL of cyclohexane to the solution until a solid substance begins to precipitate. Thereafter, heat the solution again until the solution is refluxed; cool the solution for allowing crystals to precipitate. Separate the crystals from the solution by filtration, and dry the crystals in the vacuum at the temperature between 70 and 75° C. to a constant weight. 12.28 g of intermediate II-2 is obtained, and the yield thereof is 75.0%.

II-2

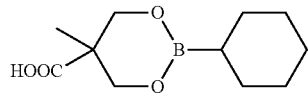

2) Add 0.32 g (1.42 mmol) of the intermediate II-2, 20 mL of dichloromethane, 0.28 g (2.18 mmol) of N,N-diisopropylethylamine, and 0.32 g (1.31 mmol) of 2,4,6-trichlorobenzoyl chloride to a 100 mL four-mouth bottle to yield a reaction solution. Stir the solution in the presence of nitrogen gas at the temperature of 14° C. for 4 h. Cool the reaction solution to the temperature of −10° C., add 1.00 g (1.09 mmol) of rapamycin and 0.27 g (2.18 mmol) of DMAP to the reaction solution, and heat the reaction solution to the temperature of 14° C. for reaction. After the reaction lasts for 14 h, add 30 mL of water to the reaction solution while stirring to form a mixture. Thereafter, transfer the mixture to a separating funnel for separating an organic phase from a water phase. Wash the organic phase by using a 2N sulfuric solution (10 mL×2), water (10 mL), a 5% sodium bicarbonate aqueous solution (10 mL), and saturated brine (10 mL), respectively, and dry the organic phase by using anhydrous magnesium sulfate. Filter, precipitate, and separate a resulting product by using silica gel column chromatography. 0.40 g of a white solid intermediate III-2 is obtained, and the yield thereof is 65.6% (according to the amount of rapamycin participating in the reaction).

III-2

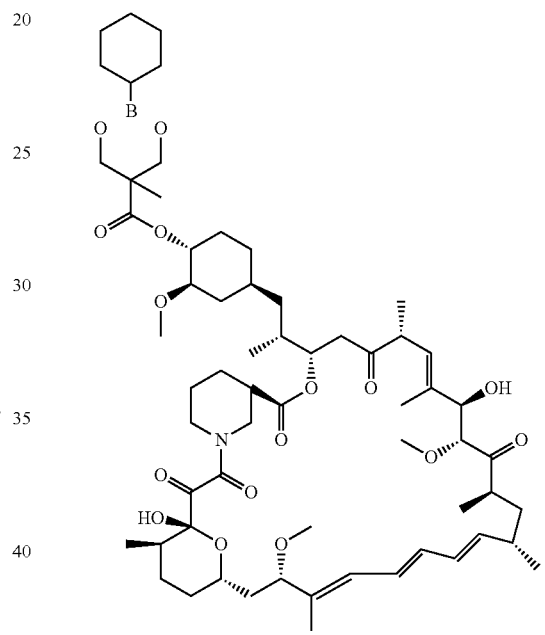

3) Add 0.45 g (0.40 mmol) of the intermediate III-2, 10 mL of tetrahydrofuran, and 2.25 g (2.0 mmol) of 2-methyl-2,4-pentanediol, respectively, to a 100 mL single-mouth bottle to yield a mixed solution. Stir the mixed solution overnight at the temperature of 0° C. for reaction. After 14 h of the reaction time, precipitate and separate a resulting product by using the silica gel column chromatography. 0.31 g of white solid temsirolimus is obtained, and a yield thereof is 76.3%.

Example 3

Add 0.24 g (1.42 mmol) of the intermediate II-1 obtained from Example 1, 20 mL of dichloromethane, 0.22 g (2.18 mmol) of triethylamine, and 0.32 g (1.31 mmol) of 2,4,6-trichlorobenzoyl chloride to a 100 mL four-mouth bottle to yield a reaction solution. Stir the solution in the presence of nitrogen gas at the temperature of 14° C. for 4 h. Cool the reaction solution to the temperature of −10° C., add 1.00 g (1.09 mmol) of rapamycin and 0.27 g (2.18 mmol) of DMAP to the reaction solution, and heat the reaction solution to the temperature of 14° C. for reaction. After the reaction lasts for 14 h, add 30 mL of water to the reaction solution while stirring to form a mixture. Thereafter, transfer the mixture to a separating funnel for separating an organic phase from a water phase. Wash the organic phase by using a 2N sulfuric solution (10 mL×2), water (10 mL), a 5% sodium bicarbonate aqueous solution (10 mL), and saturated brine (10 mL), respectively, and dry the organic phase by using anhydrous magnesium sulfate. Filter, precipitate, and separate a resulting product by using silica gel column chromatography. 0.26 g of a white solid intermediate III-1 is obtained, and the yield thereof is 65.3% (according to the amount of rapamycin participating in the reaction).

Example 4

Add 0.24 g (1.42 mmol) of the intermediate II-1 obtained from Example 1, 20 mL of dichloromethane, 0.28 g (2.18 mmol) of N,N-diisopropylethylamine, and 0.32 g (1.31 mmol) of 2,4,6-trichlorobenzoyl chloride to a 100 mL four-mouth bottle to yield a reaction solution. Stir the solution in the presence of nitrogen gas at the temperature of 14° C. for 4 h. Cool the reaction solution to the temperature of −10° C., add 1.00 g (1.09 mmol) of rapamycin and 0.18 g (2.18 mmol) of N-methylimidazole to the reaction solution, and heat the reaction solution to the temperature of 14° C. for reaction. After the reaction lasts for 14 h, add 30 mL of water to the reaction solution while stirring to form a mixture. Thereafter, transfer the mixture to a separating funnel for separating an organic phase from a water phase. Wash the organic phase by using a 2N sulfuric solution (10 mL×2), water (10 mL), a 5% sodium bicarbonate aqueous solution (10 mL), and saturated brine (10 mL), respectively, and dry the organic phase by using anhydrous magnesium sulfate. Filter, precipitate, and separate a resulting product by using silica gel column chromatography. 0.25 g of a white solid intermediate III-1 is obtained, and the yield thereof is 51.3% (according to the amount of rapamycin participating in the reaction).

Example 5

Add 0.24 g (1.42 mmol) of the intermediate II-1 obtained from Example 1, 20 mL of dichloromethane, 0.28 g (2.18 mmol) of N,N-diisopropylethylamine, and 0.32 g (1.31 mmol) of 2,4,6-trichlorobenzoyl chloride to a 100 mL four-mouth bottle to yield a reaction solution. Stir the solution in the presence of nitrogen gas at the temperature of 14° C. for 4 h. Cool the reaction solution to the temperature of −10° C., add 1.00 g (1.09 mmol) of rapamycin and 0.27 g (2.18 mmol) of DMAP to the reaction solution for reaction. After the reaction lasts for 14 h at the temperature of −10° C., add 30 mL of water to the reaction solution while stirring to form a mixture. Thereafter, transfer the mixture to a separating funnel for separating an organic phase from a water phase. Wash the organic phase by using a 2N sulfuric solution (10 mL×2), water (10 mL), a 5% sodium bicarbonate aqueous solution (10 mL), and saturated brine (10 mL), respectively, and dry the organic phase by using anhydrous magnesium sulfate. Filter, precipitate, and separate a resulting product by using silica gel column chromatography. 0.29 g of a white solid intermediate III-1 is obtained, and the yield thereof is 73.2% (according to the amount of rapamycin participating in the reaction).

Example 6

Add 0.31 g (0.287 mmol) of the intermediate III-1 obtained from Example 1, 10 mL of tetrahydrofuran, and 1.55 g (1.435 mmol) of 2-methyl-2,4-pentanediol, respectively, to a 100 mL single-mouth bottle to yield a mixed solution. Stir the mixed solution overnight at the temperature of 14° C. for reaction. After 8 h of the reaction time, precipitate and separate a resulting product by using the silica gel column chromatography. 0.23 g of a white solid temsirolimus is obtained, and a yield thereof is 76.7%.

Example 7

Add 0.31 g (0.287 mmol) of the intermediate III-1 obtained from Example 1, 10 mL of ether, and 1.55 g (1.435 mmol) of 2-methyl-2,4-pentanediol, respectively, to a 100 mL single-mouth bottle to yield a mixed solution. Stir the mixed solution overnight at the temperature of 14° C. for reaction. After 8 h of the reaction time, precipitate and separate a resulting product by using the silica gel column chromatography. 0.21 g of a white solid temsirolimus is obtained, and a yield thereof is 70.0%.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:
1. A method for synthesizing a compound of formula I,

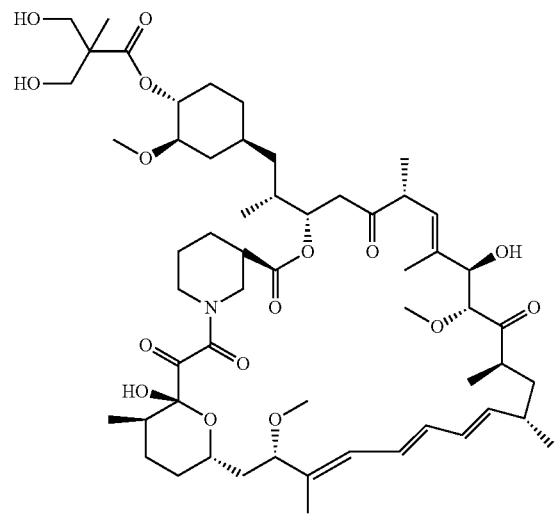

I the method comprising:
1) dissolving 2,2-dimethylol propionic acid and a substituted boric acid of formula IV:

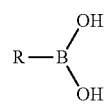

IV in tetrahydrofuran to form a solution; allowing the solution to react at room temperature; adding toluene to the solution, heating, and refluxing the solution; and adding cyclohexane to the solution to yield intermediate II represented by the following formula:

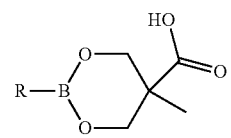

II wherein in formulae II and IV, R represents an alkyl group having between one and six carbon atoms, or a cycloalkyl group having between one and six carbon atoms;

2) dissolving the intermediate II in a first organic solvent; adding an alkali and 2,4,6-trichlorobenzoyl chloride to the first organic solvent to yield a mixture; allowing the mixture to react in the presence of nitrogen gas at a temperature of between −20 and 40° C. for between 4 and 8 h; adjusting the temperature of the mixture to −10° C.; adding rapamycin and an acid binding agent to the mixture, allowing the mixture to react overnight at room temperature; and separating a product by silica gel column chromatography to yield intermediate III represented by the following formula:

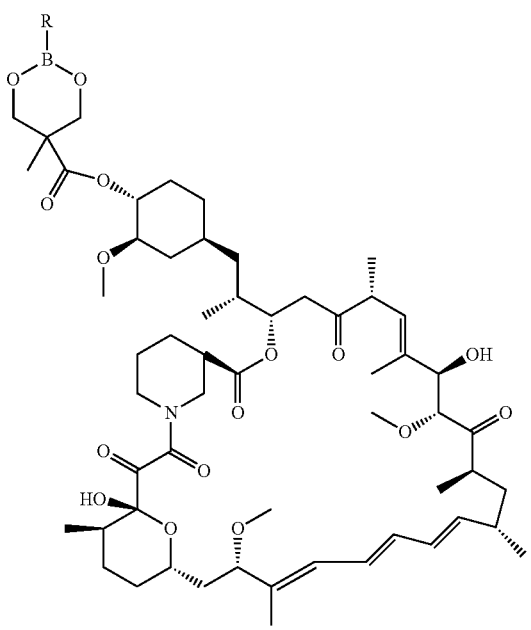

III wherein, R represents the same structure as that of the intermediate II; and 3) dissolving the intermediate III in a second organic solvent, adding a diol selected from the group consisting of 1,2-, 1,3-, 1,4-, 1,5-diol, and a $C_1$-$C_6$ alkyl substituted diol to the second organic solvent to yield a mixed solution; allowing the mixed solution to react at a temperature of between −20 and 20° C. for between 8 and 14 h; and precipitating and separating a resulting product by using silica gel column chromatography to yield the compound.

2. The method of claim 1, wherein
the substituted boric acid is selected from the group consisting of ethylboronic acid, propylboronic acid, and cyclohexylboronic acid; and
a molar ratio between 2,2-dimethylol propionic acid and the substituted boric acid is 1:1.

3. The method of claim 1, wherein in step 2),
a molar ratio between rapamicin, the intermediate II, and 2,4,6-trichlorobenzoyl chloride is 1:1-1.5:1-1.4;
the first organic solvent is selected from the group consisting of toluene, benzene, xylene, ether, methyl tert-butyl ether, tetrahydrofuran, dichloromethane, chloroform, carbon tetrachloride, 1,2-dichloroethane, and ethyl acetate;
the alkali is selected from the group consisting of triethylamine, N,N-diisopropylethylamine, and N,N-dimethylaniline; and
the acid binding agent is selected from the group consisting of pyridine, 4-dimethylaminopyridine (DMAP), 4-pyrrolidinopyridine, and N-methylimidazole.

4. The method of claim 1, wherein in step 3),
a molar ratio between the intermediate III and the diol is 1:1-10; and
the second organic solvent is selected from the group consisting of toluene, benzene, xylene, ether, methyl tert-butyl ether, tetrahydrofuran, dichloromethane, chloroform, carbon tetrachloride, 1,2-dichloroethane, ethyl acetate, and acetone.

5. The method of claim 1, wherein the diol is 2-methyl-2,4-pentanediol.

* * * * *